United States Patent
Tribastone

[19]
[11] Patent Number: 6,136,098
[45] Date of Patent: Oct. 24, 2000

[54] METHOD FOR ASPIRATING FLUID FROM AN OPERATING ROOM

[75] Inventor: Daniel N. Tribastone, Falls Church, Va.

[73] Assignee: Waterstone Medical, Inc., Falls Church, Va.

[21] Appl. No.: 09/240,055

[22] Filed: Jan. 29, 1999

[51] Int. Cl.$^7$ ............................................. B08B 5/04
[52] U.S. Cl. ................................... 134/21; 15/410
[58] Field of Search ................. 134/21; 15/410

[56] References Cited

U.S. PATENT DOCUMENTS

| | | | |
|---|---|---|---|
| 2,554,238 | 5/1951 | Burri | 15/401 |
| 3,605,171 | 9/1971 | Candor et al. | 15/322 |
| 3,626,535 | 12/1971 | Bond | 15/1.7 |
| 4,156,948 | 6/1979 | Chauvier et al. | 15/1.7 |
| 4,679,590 | 7/1987 | Hergenroeder | 137/602 |
| 4,729,404 | 3/1988 | Hergenroeder | 137/602 |
| 5,014,389 | 5/1991 | Ogilvie et al. | 15/353 |
| 5,032,184 | 7/1991 | Ogilvie et al. | 134/21 |
| 5,349,722 | 9/1994 | Chayer | 15/353 |
| 5,433,985 | 7/1995 | Atkins | 428/66.6 |
| 5,437,651 | 8/1995 | Todd et al. | 604/313 |
| 5,517,715 | 5/1996 | Monson | 15/320 |
| 5,655,258 | 8/1997 | Heintz | 15/415.1 |
| 5,720,078 | 2/1998 | Heintz | 15/415.1 |

OTHER PUBLICATIONS

Three (3) photographs, "PUD–L–SCOOP" Suction Strainer #SA35, manufactured by Simer Pump, a Rival Company, Sedalia, MO.

*Primary Examiner*—Zeinab El-Arini
*Attorney, Agent, or Firm*—Banner & Witcoff, Ltd.

[57] ABSTRACT

A method for aspirating waste fluids from the floor of an operating room. A suction head may be placed on the floor and attached to an available negative pressure source. An elongated handle is selectively engageable with the suction head. The suction head can be selectively translated across the floor or lifted and moved to a pool of waste fluid with accuracy by using the handle. While this step is being done, the length of the elongated handle protects against contamination of the operator's limbs by the fluid falling from the surgical table. The handle is easily disengaged from the suction head when the suction head is positioned in a desirable location. The suction head suctions fluid under its bottom surface. Fluid falling on the top surface of the suction head is captured and directed through peripheral holes for aspiration beneath the suction head. Fluid suctioned through the suction head is then deposited safely in a waste collection chamber.

21 Claims, 3 Drawing Sheets

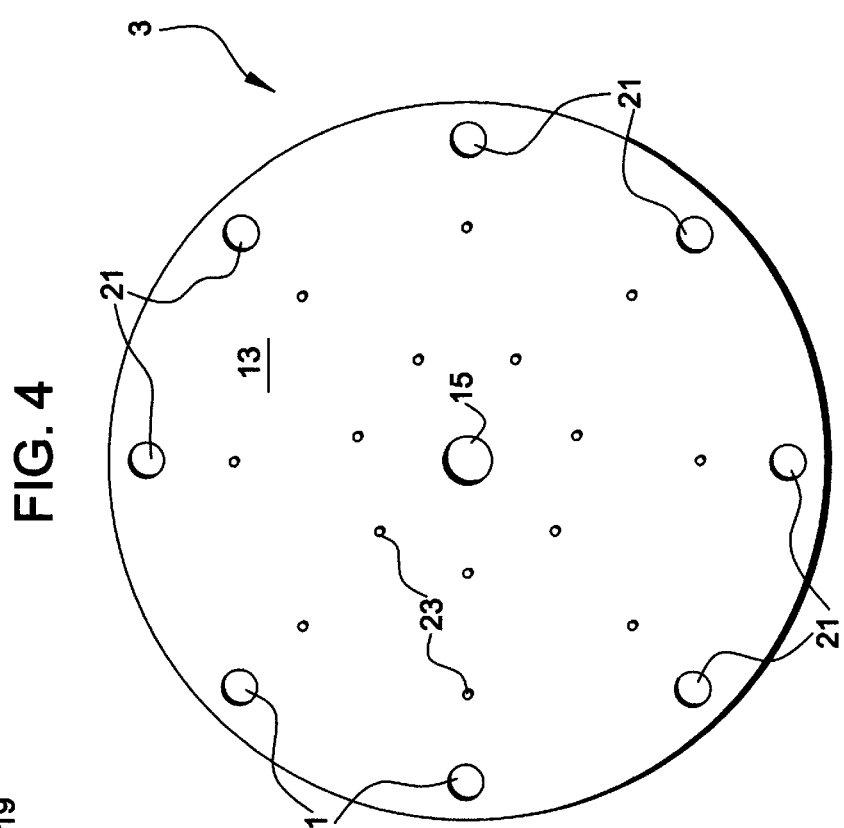
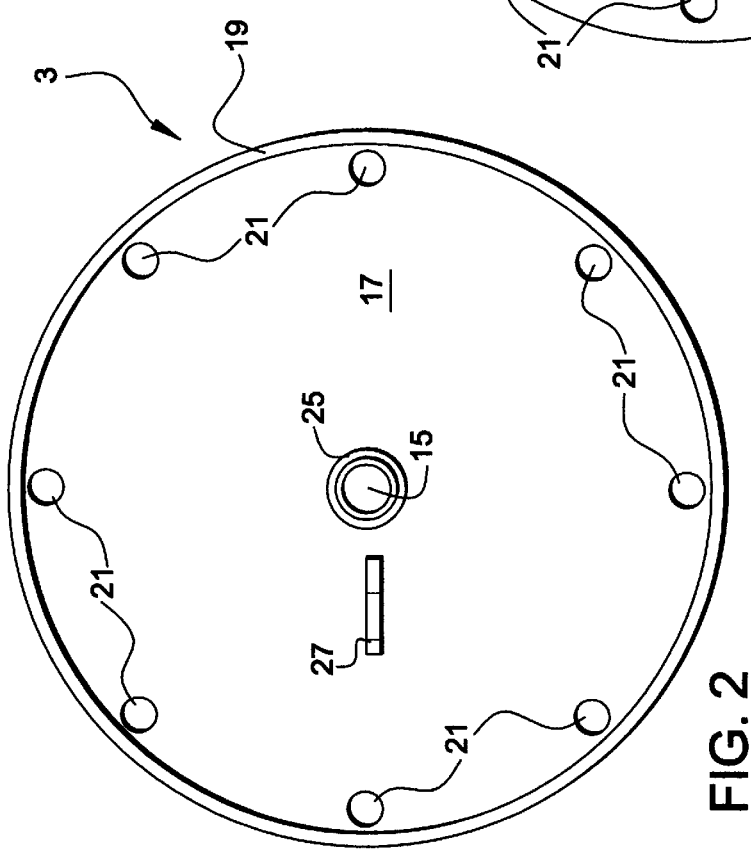
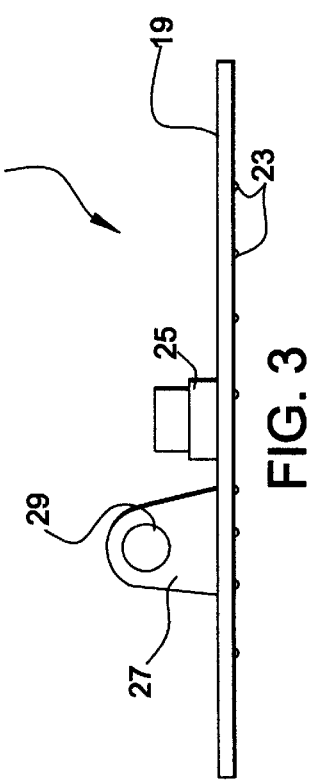

METHOD FOR ASPIRATING FLUID FROM AN OPERATING ROOM

BACKGROUND OF THE INVETON

The present invention relates to a method and apparatus for removing waste fluid that drains onto the floor of an operating room during a surgical procedure. More particularly, the invention relates to a disposable, handle-manipulated suction head that can be used with suction sources commonly found in surgical operating rooms.

During the course of a surgical procedure, especially those using arthroscopy, a fluid (such as saline) is supplied to the surgical site as a distension medium for the joint. Distension of the joint is necessary to prevent infection through an influx of airborne pathogens. Also, a steady flow of fluid past the surgical site clears blood, synovial fluid and other debris from the joint improving visibility through the arthroscopic lens. These waste fluids fall constantly to the floor during the surgery. This waste fluid, if permitted to accumulate on the floor, presents a safety hazard for operating room personnel in that they are likely to slip and fall. Also, surgical room personnel run the risk of infection from contact with the blood and synovial fluid cleared from the joint that has collected on the floor.

One attempt at solving this problem is disclosed in U.S. Pat. Nos. 4,679,590 and 4,729,404. These patents disclose a rubber mat having a plurality of channels for receiving and directing the hazardous fluid. The mats are adapted for placement beneath a surgical site in sealed engagement with the floor. The top surface of the mat is configured as multiple inverted pyramidal elements for collecting waste fluid and directing it to a drain hole on the bottom side of the mat. The bottom side of the mat is provided with flow channels that converge to a common suction port that can be connected to wall-mounted suction ports commonly available in surgical operating rooms. The suction delivers the recovered waste fluid to a canister for disposal.

Although the suction mat arrangement described above is capable of removing waste fluid that falls on the mat, it cannot drain the rather significant amount of waste fluid that does not fall on it and results in a slip and fall hazard. During arthroscopic surgery the sterile fluid delivered to the surgical site is often delivered at relatively high pressures making it difficult for surgical personnel to anticipate the spray pattern of the waste fluid and place the mat in a position where it will capture all of the waste fluid that falls to the floor. Also, the mat has a relatively fixed arrangement that is hard to lift and place in a different position if the site of spillage changes.

Another approach has included the use of some commercially available vacuum cleaners that are connected to their own waste collection chamber and suction source. The suction heads on the commercially available vacuum cleaners may be manipulated to access a wide area of the floor. A problem with commercially available vacuum cleaners, however, is that the suction head must be held at the correct angle to suction the waste fluid effectively and therefore must be attended constantly. Further, these vacuum cleaners and their suction source and waste collection chamber are typically large and bulky, which restricts the movement of surgical personnel and distracts them from their surgical duties. Also, the motor for generating the suction source is loud and inhibits verbal communication between surgical room personnel. The prior art has also noted that conventional vacuum cleaners are not suitable for use in an operating room because the vacuum cleaner requires constant attention to be effective and are otherwise unsuitable for operating room conditions.

U.S. Pat. Nos. 5,014,389 and 5,032,184 to Ogilvie et al. disclose another approach to collecting waste fluids that fall to the floor of the operating room. These Ogilvie patents disclose a method for aspirating waste fluids from a surgical operating room utilizing a suction head without a handle. Instead, the Ogilvie suction head slides along a floor in response to translation forces applied by the foot of operating room personnel. There are several drawbacks to this foot positioned suction head. The foot positioning of this suction head requires the operating room personnel to place their leg and foot in the flow of the falling waste fluid. This places the personnel at an increased risk of contracting a viral or bacterial infection from blood-borne pathogens. The effective range and accuracy of foot positioning is limited by the personnels reach and any attempt at gaining extra range with one or both feet on a slippery surface poses a further slip-and-fall hazard. Additionally, the lack of a handle on this suction head makes it difficult the lift from the floor for movement to separate puddles without contaminating the hands of the operator. Dragging the suction head from one puddle to the next only results in smearing of the first puddle and further contamination of the floor. Another drawback of the Ogilvie suction head is that it has a large contact surface on its bottom that makes it difficult to translate the suction head across the floor. The large contact area and the suction forces result in a significant amount of friction between the bottom of the suction head and the floor causing the suction head to stick to the floor. The suction head's tendency to stick to the floor also makes it difficult to lift from the floor for movement over the top of the various cords, feet and other obstacles encountered in the operating room.

SUMMARY OF THE INVENTION

Accordingly, it is a primary object of the present invention to provide a method and apparatus for selectively aspirating waste fluid from the floor of an operating room while the risk of exposure to infection from the waste fluid.

It is another object of the present invention to provide a method and apparatus for accurately aspirating waste fluid out of a person's reach with a foot or hand from the floor of an operating room by providing an elongated handle with which to manipulate the suction head.

It is still another object of the present invention to provide a method and apparatus with a suction head attached to a removable handle so that the suction head may be horizontally translated to different locations, with or without lifting it from the floor, and then placed in position to suction an ongoing spill of waste fluid.

It is still another object of the present invention to provide a method and apparatus with a suction head including a plurality of spacers attached to its bottom surface so that clearance is maintained between the bottom surface and the floor for easy horizontal translation along the floor and to prevent the suction head from sticking to the floor.

These and other objects are accomplished in accordance with the present invention by a method and apparatus for aspirating waste fluid from a floor surface in a surgical operating room. The method of aspirating waste fluid includes providing a suction head, an elongated handle and flexible suction tubing. The suction head is placed in fluid communication with a source of negative pressure using the flexible suction tubing. The suction head is placed on the surgical operating room floor. The elongated handle engages the suction head. An application of force to the handle moves the suction head within the surgical operating room and waste fluid is aspirated through the suction head.

In another aspect, the method of aspirating waste fluid includes providing a suction head, an elongated handle and flexible suction tubing. The suction head is connected to a source of negative pressure by positioning the flexible suction tubing between the suction head and the source of negative pressure. The suction head is placed on the surgical room floor. The aspirating unit is moved by grasping the elongated handle, applying a force to the suction head through the elongated handle and positioning the suction head in the waste fluid. The waste fluid is aspirated through the suction head and the flexible suction tubing for collection.

In still another aspect the apparatus for aspirating waste fluid from a surgical operating room floor includes a suction head, a handle and flexible suction tubing. The suction head has a top surface, a bottom surface and a suction port. The top surface of the suction head includes a rim defining the periphery of the top surface and a plurality of drain holes positioned about the periphery. The drain holes extend between the top and bottom surfaces and serve to drain the fluid collected on the top surface through to the bottom surface. The bottom surface includes a plurality of spacers extending from its bottom surface and serving to position the bottom surface above the operating room floor. The suction port defines an aperture extending between the top and bottom surface that serves to supply suction to the bottom surface. The handle is engageable with the suction head and permits movement of the suction head by an application of force to the handle. The flexible suction tubing connects the suction port of the suction head in fluid communication with an existing negative pressure source during the operation of the aspirating unit.

The above and other objects, features and advantages of the present invention will be readily apparent and filly understood from the following detailed description of preferred embodiments, taken in connection with the appended drawings.

BRIIEF DESCRIPTION OF THE DRAWINGS

FIG. 2 is a top plan view of the suction head shown in FIG. 1 disengaged from the elongated handle and the flexible suction tubing.

FIG. 3 is a side elevation view of the suction head shown in FIG. 2.

FIG. 4 is a bottom plan view of the suction head shown in FIG. 2.

DETAILED DESCRIPTION OF THE PREFERRED EMBODIMENTS

Figure 1:
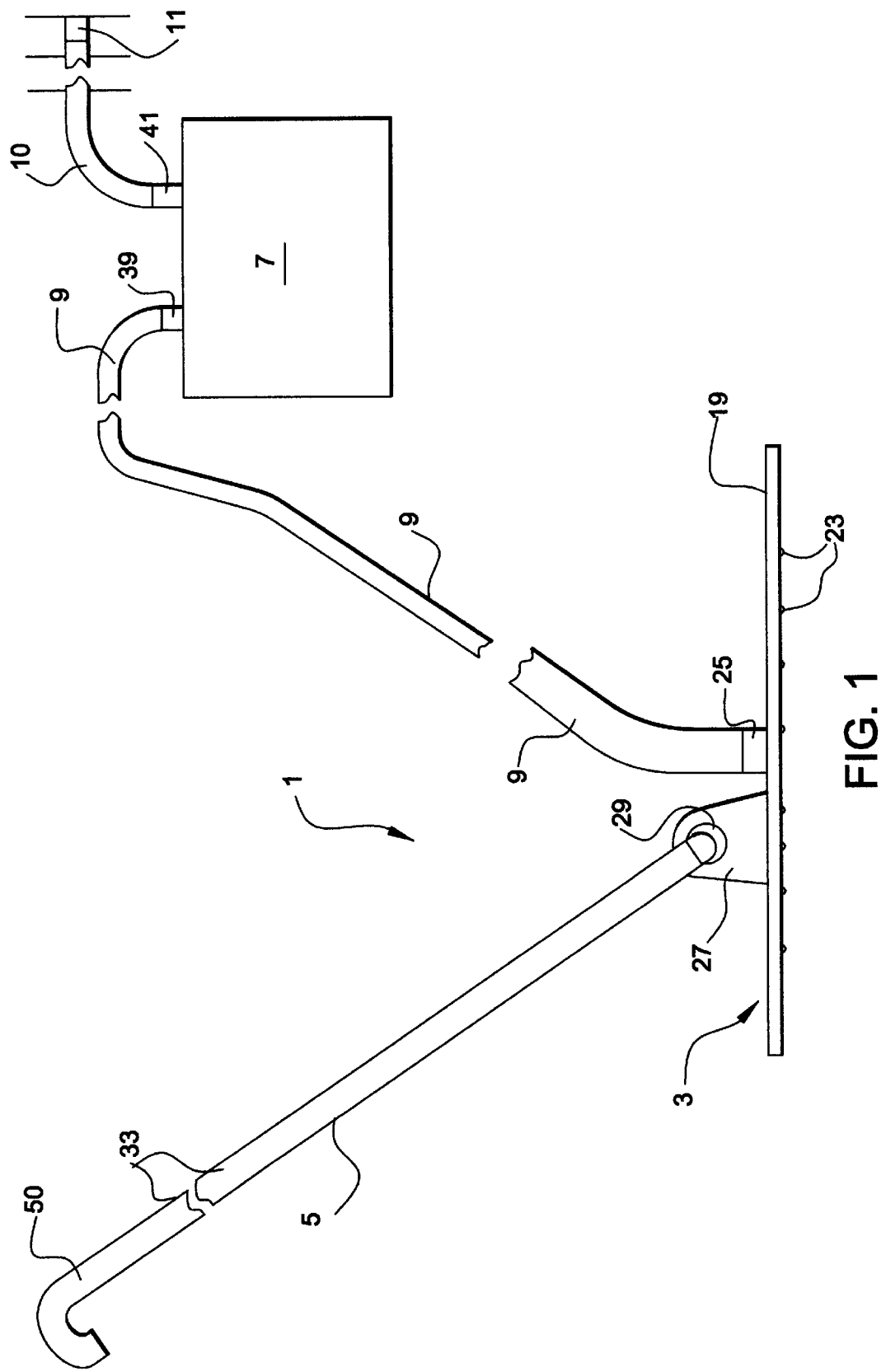
FIG. 1 is a side elevational view of the aspirating unit showing the elongated handle engaged with the suction head and the suction head connected by flexible suction tubing to a waste collection chamber and a negative pressure source.

Referring to FIGS. 1–8 of the accompanying drawings, an aspirating system 1 according to the present invention includes a suction head 3 and a rigid, elongated handle 5 for coupling to suction head 3. The suction head 3 is connected to a waste collection chamber 7 through flexible suction tubing 9. The waste collection chamber 7 is in turn connected by a second flexible suction tubing 10 to a source 11 of negative pressure. Aspiration of waste fluid on a surgical room floor is accomplished by placing suction head 3 on the floor and engaging suction head 3 with handle 5. Applying a force to handle 5 translates suction head 3 to a desired location on the floor such as one covered with, or expected to be covered with, waste fluid or underneath an ongoing spill. Waste fluid is aspirated by suction from the negative pressure source 11, suctioning waste fluid from below suction head 3 towards and through an aperture 15 in the bottom surface 13. Waste fluid from an ongoing spill is also collected on a top surface 17 of suction head 3. A retaining lip 19 around the periphery of top surface 17 aids in the disposal of the waste fluid by preventing the waste fluid from flowing away from the suction head 3 until it is suctioned through drain holes 21 to the bottom of the suction head 3 where the waste fluid is aspirated by the negative pressure source 11 to the collection chamber 7.

In a preferred embodiment, suction head 3, as shown in FIGS. 1–4, is in the shape of a circular disk with retaining lip 19 forming a short wall around the outer circumference of the circular disk and enclosing top surface 17. Since suction head 3 is in the shape of a circular disk drain holes 21 can be regularly spaced and equidistant from each other to promote even waste fluid flow through drain holes 21 and to prevent pooling in a comer. In a preferred embodiment the diameter of suction head 3 is 8 inches, but in other preferred embodiments may vary from 3 to 12 inches. Other shapes and sizes for suction head 3, such as a square, rectangle or more irregular shapes may be used but may not have the above mentioned advantages. The drain holes 21 are preferably 3/16 of an inch in diameter. Drain holes are located on the periphery of the circular disk to maintain the negative pressure under the bottom surface 13. Additional drain holes of varying shapes, diameters and locations may be added to enhance waste fluid flow through top surface 17. However, variation in drain holes 21 may result in decreased suction pressure under bottom surface 13 and may affect its effective area of suction by disrupting flow into aperture 15.

Retaining lip 19 only requires a short wall because ongoing spillage is being rapidly aspirated before it has a chance to overfill top surface 17. Also, the low profile of retaining lip 19 allows portions of large spills to overflow onto the top surface 17 for retention when the suction head 3 is thrust by handle 5 into the large spill. Retaining lip 19 may be varied in height depending upon the expected amount of waste fluid flow and the desired amount of waste fluid retention, especially for waste fluids with higher viscosities. The top surface 17 of suction head 3 as shown in FIG. 1 is smooth and has a slight downward slope from aperture 15 to its outer periphery to promote the flow of fluid. The downward slope of top surface 17 may be increased to further promote the flow of contaminated fluid to its outer periphery and through drain holes 21.

The bottom surface 13 of suction head 3 is shown best in FIG. 3 as the bottom surface of a circular disk. The disk shape of the suction head 3 allows an even distribution of the suction pressure under bottom surface 13 because the periphery of suction head 3 is equidistant at all points from aperture 15. If desired, other shapes such as a triangle or square may be used but at a subsequent loss of the even negative pressure distribution.

Figure 8:
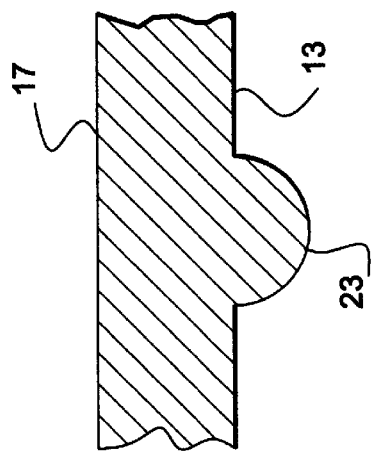
FIG. 8 is a partial cross-sectional view of the spacers mounted on the bottom surface of the suction head shown in FIGS. 1–4.
Figure 5:
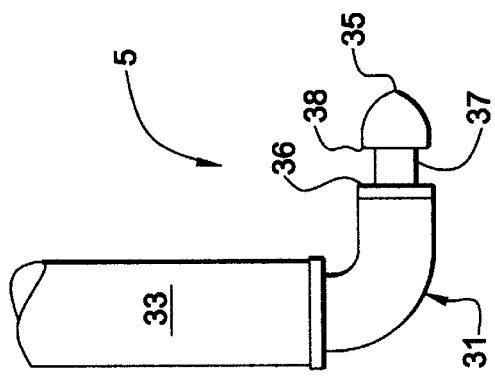
FIG. 5 is a side elevational view of the suction head coupling at the end of the elongated handle shown in FIG. 1 disengaged from the suction head.
Figure 7:
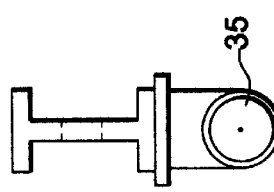
FIG. 7 is a front elevational view of the suction head coupling removed from the long tube shown in FIGS. 5 and 6.
Figure 6:
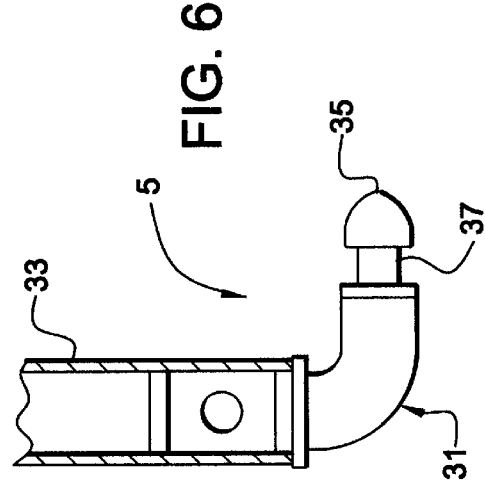
FIG. 6 is a partial cross-sectional view of the suction head coupling revealing the connection arrangement between the long tube and suction head coupling of the handle shown in FIG. 1.

Suction head 13 includes a plurality of gliders or spacers 23 extending from its bottom surface 13 as shown in FIG. 8. The spacers 23 allow clearance between bottom surface 13 and the floor, thus permitting a smooth suction of waste fluid into aperture 15 and waste fluid flow through drain holes 21 from top surface 17. In the preferred embodiment, spacers 23 are small hemispheres with curved lower surfaces that take up a minimal amount of surface area on the bottom surface 13. As well as permitting maximum waste fluid suctioning, the small size and the distribution of the spacers 23 reduces the tendency for the suction head 3 to bind to the floor. The small size of the spacers 23 also minimizes the surface area of the gliders 23 in contact with the operating room floor which minimizes the friction that resists sliding of the suction head 3. In a preferred embodiment the size of the gliders or spacers 23 are 0.02 inches in height. In other preferred embodiments spacers may range from as small as 0.005 to 0.03 inches in height depending upon the desired amount of clearance between bottom surface 13 and the floor. The distribution of the glider/spacers 23 may vary with the suction pressure to prevent binding, but preferably several are near the aperture 15 of bottom surface 3 where suction forces are at their highest to prevent the center from collapsing into contact with the floor. Preferably suction head 3 is integrally constructed of polypropylene plastic that is injection molded. This plastic is light, inexpensive yet stiff enough to stand up under vigorous use. However, other types of plastics such as polystyrene may be used. Heavier materials, however, may not have the above advantages.

Aperture 15 is a circular hole 0.25 inches in diameter extending from the top surface 17 to the bottom surface 13 and providing fluid communication therebetween. Suction port 25 is a circular tube with an inside diameter equal to aperture 15. Suction port 25 is connected on its bottom edge to top surface 17 and surrounds the periphery of aperture 15. The suction port 25 has an outside diameter the same as the inside diameter of flexible suction tubing 9 and serves as a connection for flexible suction tubing 9. The elastic nature of flexible suction tubing 9 allows it to be press-fit over suction port 25. The other end of flexible suction tubing 9 is connected to a negative pressure source 11 with waste collection chamber 7 fluidly interposed therebetween. Thus, waste fluid under bottom surface 13 is suctioned into aperture 15 through suction port 25, into flexible suction tubing 9 and into a waste collection chamber 7 at the end of flexible suction tubing 9. Any number of standard connections may be used to provide a connection for flexible suction tubing 9, but suction port 25 provides a simple and firm connection. Aperture 15 and suction port 25 may be varied in size to fit the available flexible suction tubing 9 and the negative pressure source 11.

In the preferred embodiment, suction head 3 includes a handle coupling 27 in the shape of a rounded fin emanating from top surface 17. The handle coupling 27 includes a circular coupling hole 29 preferably 7/16 of an inch in diameter. This coupling interfaces with the handle 5. FIGS. 4–7 illustrate the elongated handle 5. Elongated handle 5 includes a long tube 33 constructed of a rigid and lightweight material such as polypropylene plastic and ending in a suction head coupling 31. The suction head coupling 31 is secured within the long tube 33 and is also constructed of a rigid and lightweight material. Suction head coupling 31 and tube 33 may be integrally manufactured or separately manufactured and assembled using a cotter pin or some other common connection. The suction head coupling 31 has the shape of a hook that bends at a right angle to the axis of tube 33 and ends in a tapered bulb 35 with a neck 37. The diameter of the base of tapered bulb 35 is preferably 3/8 of an inch. The front of the bend and the rear of the bulb 35 have respective opposing flanges 36 and 38 on opposite sides of the neck 37.

The elongated handle 5 engages with suction head 3 by inserting tapered bulb 35 through coupling hole 29 in handle coupling 27. The 1/16 of an inch difference in diameter between tapered bulb 35 and coupling hole 29 allows for easy engagement and disengagement. Different amounts of clearance could also be used. The tapered end of tapered bulb 35 facilitates the engagement of handle coupling 27 and the suction head coupling 31. The inner edge of coupling hole 29 seats into neck 37 between flanges 36 and 38 on the suction head coupling 31. Flanges 36 and 38 serve to restrain the relative movement between handle coupling 27 and suction head coupling 31 to allow the transmission of forces through elongated handle 5 to suction head 3. If desired, alternative handle configurations, such as a U-shaped, L-shaped, or J-shaped hook, may be used in lieu of the depicted coupling. Also the elongated handle 5 may include a handle hook 50 either integrally formed with tube 5 or manufactured separately and attached in a manner similar to suction head coupling 31.

During operation, suction head 3 is connected to a source of negative pressure 11 enabling the suction head 3 to aspirate waste fluids from the operating room floor. Flexible suction tubing 9 is connected to suction port 25 by hand fitting flexible suction tubing 9 over the outside diameter of suction port 25. As mentioned above, the inside diameter of the suction tubing 9 and the outside diameter of the suction port 25 are configured to allow a press fit. The length of suction tubing 9 may be customized for the desired reach of the aspirating unit. The suction tubing 9 may also be made of varying materials depending upon the flexibility and toughness needed for different operating room environments. The other end of suction tubing 9 is connected to an inlet port 39 of the waste collection chamber 7 located above the waste collection chamber's bottom. A second suction tubing 10 is connected to the waste collection chamber's 7 outlet port 41 and the wall-mounted negative pressure source 11.

The negative pressure source 11 creates a flow of waste fluid and air from below the suction head 3 through suction tubing 9 and into the waste collection chamber 7. The difference in height between the base of the waste collection chamber and the inlet port 39 permits the waste fluid to fall to the bottom of the waste collection chamber 7 and the air to flow through to the outlet port 41 which is directly connected by the second suction tubing 10 to the wall-mounted negative pressure source 11. This prevents contaminated fluid from entering the hospital vacuum source. A range of commercially available waste collection chambers of this type are well known in the art, and one such preferred device is disclosed in U.S. Pat. No. 5,792,126 assigned to Waterstone Medical, Inc and herein incorporated by reference.

The operating suction head 3 is placed upon the surgical room floor with the gliders/spacers 23 on its bottom surface 13 in contact with the floor. The tube 33 of elongated handle 5 is grasped by hand at the top end with the suction head coupling 31 at the bottom. The length of tube 33 of elongated handle 5 may be increased depending upon the reach needed by the operator and also to decrease the risk of the waste fluid splashing and causing further contamination of the operator's limbs.

The handle coupling 27 emanating from top surface 17 of the suction head 3 is then engaged with suction head coupling 31 by inserting tapered bulb 3 through the coupling hole 29 from either side in handle coupling 27. The radial direction of the fin shape of handle coupling 27 allows insertion of tapered bulb 35 through either side of handle coupling 27 without obstruction by suction tubing 9. Lifting elongated handle 5 seats the edge of coupling hole 29 in the neck 37 between the two vertical flanges 36 and 38. The coupling hole 29 can also be seated between the two vertical flanges 36 and 38 by lowering or rotating the top of elongated handle 5.

Once seated, forces applied to the elongated handle 5 are transmitted to suction head 3 or to translate suction head 3 across the floor, with or without lifting, until suction head 3 is in a puddle of waste fluid or in a position to catch waste fluid falling from the operating table. In the case of an ongoing cascade of bio-hazardous waste fluid from the operating table, the length of elongated handle 5 prevents unnecessary contamination of the operator's limbs by facilitating placement of the suction head 3 in various locations in the operating room, such as beneath an operating table. The ability to lift and set suction head 3 accurately in different positions prevents the smearing of the waste fluid across the floor and allows the suction head 3 to be lifted over cords, feet and other obstacles common to a surgical operating room. Once suction head 3 is placed within a pool of waste fluid or under waste fluid failing from the operating table, it will aspirate the waste fluid from the floor. Waste fluid between bottom surface 13 and the floor is drawn radially inward to suction port 25 through the clearance left between bottom surface 13 and the floor due to the presence of spacers 23. Waste fluid is drawn by suction up through suction port 25 and into suction tubing 9 until deposited within the waste collection chamber.

Elongated handle 5 can be easily disengaged from suction head 3 by removing the suction head coupling 31 from handle coupling 27. Disengagement of elongated handle 5 from suction head 3 allows elongated handle 5 to be removed from the vicinity of personnel performing the surgery and subsequently allowing them movement unencumbered by the handle. If it is desired to move suction head 3 again, elongated handle 5 may be re-engaged for further movement and disengaged again as often as desired. During arthroscopic surgery the angle and position of the fluid being supplied to the joint is subject to change, which changes the position from which the fluid falls from the joint and table. Sometimes this necessitates the frequently engagement, disengagement and re-engagement of the handle 5 with suction head 3.

At the end of the procedure, elongated handle 5 may be disposed of with the suction head 3, or alternatively, it may be cleaned and sanitized with disinfectant solution to prevent further contamination by its contact with clean surfaces and for reuse with a new suction head 3. Suction head 3 is disposed of by using elongated handle 5 to lift suction head 3 and place it in a biohazard bag or over a disposal bin or chute for disposal without exposing the operating room personnel to potential contamination by hand contact. After cleaning and disinfecting the handle 5 may be hung by hook handle 50 on a collection chamber 7, ring stand, hook, bar or the like.

The present invention has been described in terms of preferred and exemplary embodiments thereof. Numerous other embodiments, modifications and variations within the scope and spirit of the appended claims will occur to persons of ordinary skill in the art.

What is claimed is:

1. A method of aspirating waste fluid from a surgical operating room having a floor comprising the steps of:
   providing a suction head, an elongated handle and a flexible suction tubing;
   placing the suction head in fluid communication with a source of negative pressure using the flexible suction tubing;
   placing the suction head on the surgical operating room floor;
   engaging the suction head with the elongated handle;
   moving the suction head within the surgical operating room by applying a force to the elongated handle; and
   aspirating the waste fluid through the suction head;
   wherein said engaging step includes the steps of gasping the elongated handle and coupling an elongated handle coupling portion on the suction head with a suction head coupling portion on the handle; and
   wherein said coupling step includes the step of inserting a tapered bulb of the suction head coupling portion through a coupling hole on the elongated handle coupling portion.

2. The method of aspirating waste fluid according to claim 1, wherein said coupling step further includes the step of seating an inner edge of the coupling hole behind the tapered bulb, between a pair of opposing flanges and on a neck of the suction head coupling portion.

3. The method of aspirating waste fluid according to claim 2, wherein said moving step includes the step of lifting the suction head off of the operating room floor, translating the suction head relative to the operating room floor and again placing the suction head on the floor.

4. The method of aspirating waste fluid according to claim 2, wherein said moving step includes the step of horizontally translating the suction head along the operating room floor.

5. The method of aspirating waste fluid according to claim 4, wherein the handle includes a longitudinal axis, and said moving step includes the step of applying pressure along the longitudinal axis of the handle and leaving the flexible suction tubing free of direct pressure.

6. The method of aspirating waste fluid according to claim 5, further comprising the step of disengaging the elongated handle from the suction head.

7. The method of aspirating fluid according to claim 6, wherein said disengaging step further includes the step of uncoupling the suction head coupling portion from the handle coupling portion by removing the tapered bulb from the coupling hole.

8. The method of aspirating waste fluid according to claim 7, further comprising the steps of reengaging the elongated handle with the suction head and again moving the suction head within the operating room by applying force to the elongated handle.

9. The method of aspirating waste fluid according to claim 8, wherein said reengaging step includes the steps of recoupling the suction head coupling portion with the handle coupling portion by reinserting the tapered bulb into the coupling hole.

10. The method of aspirating waste fluid according to claim 8, further comprising the steps of collecting waste fluid on a top surface of the suction head and retaining the waste fluid within a retaining lip on the top surface and draining the waste fluid on the top surface through a plurality of drain holes in the suction head to the bottom surface of the suction head.

11. The method of aspirating waste fluid according to claim 1, wherein said step of aspirating waste fluid through the suction head includes suctioning the waste fluid between a bottom surface of the suction head and the floor and suctioning the waste fluid through an aperture in the bottom surface of the suction head.

12. The method of aspirating waste fluid according to claim 1, further comprising collecting aspirated waste fluid in a waste collection chamber.

13. The method of aspirating waste fluid according to claim 12, wherein said collecting step further includes the steps of connecting the suction tubing between a suction port of the suction head and an inlet port located above the bottom of the waste collection chamber;

connecting a suction tubing between an outlet port located above the bottom of the waste collection chamber and the source of the negative pressure;

creating a flow of air through the waste collection chamber from the inlet port to the outlet port; and said creating a flow of air step includes the step of permitting the waste fluid that is carried by the flow of air to fall to a bottom of the chamber.

14. A method of aspirating waste fluid from a surgical operating room having a floor comprising the steps of:

providing a suction head, an elongated handle and a flexible suction tubing;

placing the suction head in fluid communication with a source of negative pressure using the flexible suction tubing;

placing the suction head on the surgical operating room floor;

engaging the suction head with the elongated handle;

moving the suction head to a different location on the surgical operating room floor by applying a force to the elongated handle;

disengaging the elongated handle from the suction head;

aspirating the waste fluid through the suction head; and repeating said engaging, moving, and disengaging steps to aspirate the waste fluid from different locations in the surgical operating room.

15. The method of aspirating waste fluid according to claim 14, wherein said engaging step includes the step of inserting a tapered bulb of the elongated handle through a coupling hole in the suction head.

16. The method of aspirating waste fluid according to claim 15, wherein said engaging step further includes the step of seating an inner edge of the coupling hole behind the tapered bulb, between a pair of opposing flanges and on a neck of the suction head.

17. The method of aspirating waste fluid according to claim 14, wherein said moving step includes the step of lifting the suction head off of the operating room floor, translating the suction head relative to the operating room floor and again placing the suction head on the floor.

18. The method of aspirating waste fluid according to claim 14, wherein said moving step includes the step of horizontally translating the suction head along the operating room floor.

19. The method of aspirating waste fluid according to claim 18, wherein said moving step includes the step of applying pressure along a longitudinal axis of the handle and leaving the flexible suction tubing free of direct pressure.

20. The method of aspirating waste fluid according to claim 14, wherein said step of aspirating waste fluid through the suction head includes suctioning the waste fluid between a bottom surface of the suction head and the floor and suctioning the waste fluid through an aperture in the bottom surface of the suction head.

21. The method of aspirating waste fluid according to claim 20, further comprising the steps of collecting waste fluid on a top surface of the suction head, retaining the waste fluid within a retaining lip on the top surface, and draining the waste fluid on the top surface through a plurality of drain holes in the suction head to the bottom surface of the suction head.

* * * * *

UNITED STATES PATENT AND TRADEMARK OFFICE
CERTIFICATE OF CORRECTION

PATENT NO.: 6,136,098
DATED: October 24, 2000
INVENTOR: Daniel N. TRIBASTONE

It is certified that errors appear in the above-identified patent and that said Letters Patent is hereby corrected as shown below:

column 2, line 17:
"personnels" should be replaced with --personnel's-- column, 2, line 38:
--minimizing-- should be inserted after "while"

column 3, line 37:
"filly" should be replaced with --fully-- column 4, line 36:
"comer" should be replaced with --corner--

, column 7, line 36:
"failing" should be replaced with --falling--

In Claim 1, column 8, line 18:
"gasping" should be replaced with --grasping--

Signed and Sealed this

Twenty-second Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,136,098  
DATED : October 24, 2000  
INVENTOR(S) : Daniel N. Tribastone It is certified that error appears in the above-identified patent and that said Letters Patent is hereby corrected as shown below:

Column 2,  
Line 17, "personnels" should be replaced with -- personnel's --  
Line 38, -- minimizing -- should be inserted after "while"

Column 3,  
Line 37, "filly" should be replaced with -- fully --

Column 4,  
Line 36, "comer" should be replaced with -- corner --

Column 7,  
Line 36, "failing" should be replace with -- falling --

Column 8,  
Line 18, "gasping" should be replaced with -- grasping --

Signed and Sealed this

Twenty-first Day of January, 2003

JAMES E. ROGAN  
*Director of the United States Patent and Trademark Office*